US012747340B2

(12) United States Patent
Iwadate et al.

(10) Patent No.: US 12,747,340 B2
(45) Date of Patent: Sep. 29, 2026

(54) CELLULOSE PARTICLES

(71) Applicant: FUJIFILM Business Innovation Corp., Tokyo (JP)

(72) Inventors: Yuko Iwadate, Kanagawa (JP); Hideaki Yoshikawa, Kanagawa (JP); Satomi Kashiwagi, Kanagawa (JP); Kenji Yao, Kanagawa (JP); Tetsuya Taguchi, Kanagawa (JP); Hirokazu Hamano, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 278 days.

(21) Appl. No.: 18/460,703

(22) Filed: Sep. 5, 2023

(65) Prior Publication Data

US 2024/0327617 A1 Oct. 3, 2024

(30) Foreign Application Priority Data

Mar. 29, 2023 (JP) ................................ 2023-054185

(51) Int. Cl.

| | |
|---|---|
| ***C08L 1/02*** | (2006.01) |
| ***A61K 8/02*** | (2006.01) |
| ***A61K 8/73*** | (2006.01) |
| ***A61Q 19/00*** | (2006.01) |

(52) U.S. Cl.

CPC .............. *C08L 1/02* (2013.01); *A61K 8/0241* (2013.01); *A61K 8/731* (2013.01); *A61Q 19/00* (2013.01)

(58) Field of Classification Search

CPC ......... C08L 1/02; A61K 8/0241; A61K 8/731; A61Q 19/00; C08J 3/12

See application file for complete search history.

(56) References Cited

U.S. PATENT DOCUMENTS

| | | | | |
|---|---|---|---|---|
| 2020/0360261 | A1 | 11/2020 | Imoto | |
| 2022/0054367 | A1 | 2/2022 | Imoto et al. | |
| 2023/0301897 | A1 * | 9/2023 | Kobayashi | A61K 8/731 |
| 2024/0247112 | A1 * | 7/2024 | Abe | C08L 1/14 |

FOREIGN PATENT DOCUMENTS

| | | |
|---|---|---|
| EP | 4180092 | 5/2023 |
| EP | 4209514 | 7/2023 |
| JP | H02222401 | 9/1990 |
| WO | 2019151486 | 8/2019 |
| WO | 2020054810 | 3/2020 |
| WO | 2022014463 | 1/2022 |
| WO | 2022050004 | 3/2022 |

OTHER PUBLICATIONS

"Search Report of Europe Counterpart Application", issued on Mar. 5, 2024, p. 1-p. 8.

"Office Action of Europe Counterpart Application", issued on Feb. 25, 2025, p. 1-p. 4.

* cited by examiner

*Primary Examiner* — Sue X Liu
*Assistant Examiner* — Susannah S Armstrong
(74) *Attorney, Agent, or Firm* — JCIPRNET

(57) ABSTRACT

Solid cellulose particles contain cellulose as a main component. The cellulose particles have a volume average particle diameter D of from 1 μm to 30 μm inclusive and a circularity of 0.86 or more. A value A represented by the following formula (1) is less than 0.15: (wherein, in formula (1), D is the volume average particle diameter (μm) of the cellulose particles, and S is a BET specific surface area ($m^2/g$) of the cellulose particles).

$$A = 1/(D \times S) \quad \text{formula (1)}$$

10 Claims, No Drawings

CELLULOSE PARTICLES

CROSS-REFERENCE TO RELATED APPLICATIONS

This application is based on and claims priority under 35 USC 119 from Japanese Patent Application No. 2023-054185 filed Mar. 29, 2023.

BACKGROUND

(i) Technical Field

The present disclosure relates to cellulose particles.

(ii) Related Art

Japanese Unexamined Patent Application Publication No. 2-222401 proposes "a method for controlling the size of fine pores in a cellulose material. The method is characterized in that the cellulose material is treated with a liquid treatment agent having the ability to swell a cellulose raw material."

International Publication No. WO 2019/151486 proposes "a particle containing cellulose or a cellulose derivative as a main component. The particle has a surface having a wrinkle-like or fold-like uneven structure, and the crystallization degree of the particle is 80% or less."

International Publication No. WO 2020/054810 proposes "a particle that has a surface having an uneven structure and contains cellulose or a cellulose derivative and a clay mineral as main components."

SUMMARY

Aspects of non-limiting embodiments of the present disclosure relate to cellulose particles containing cellulose as a main component. The cellulose particles have better spreadability, adsorption ability, and sustained component release performance than cellulose particles which have a volume average particle diameter D of less than 1 m or more than 30 m or a circularity of less than 0.86 or in which a value A represented by formula (1) below is 0.15 or more.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there are provided solid cellulose particles containing cellulose as a main component, wherein the cellulose particles have a volume average particle diameter D of from 1 μm to 30 μm inclusive and a circularity of 0.86 or more, and wherein a value A represented by the following formula (1) is less than 0.15:

$$A = 1/(D \times S) \qquad \text{formula (1)}$$

(wherein, in formula (1), D is the volume average particle diameter (μm) of the cellulose particles, and S is a BET specific surface area ($m^2/g$) of the cellulose particles).

DETAILED DESCRIPTION

An exemplary embodiment of the present disclosure will be described below. The following description and Examples are illustrative of the exemplary embodiment and are not intended to limit the scope of the present disclosure.

In a set of numerical ranges expressed in a stepwise manner in the present specification, the upper or lower limit in one numerical range may be replaced with the upper or lower limit in another numerical range in the set of numerical ranges expressed in a stepwise manner. Moreover, in a numerical range described in the present specification, the upper or lower limit in the numerical range may be replaced with a value indicated in an Example.

Any component may contain a plurality of materials corresponding to the component.

When reference is made to the amount of a component in a composition, if the composition contains a plurality of materials corresponding to the component, the amount means the total amount of the plurality of materials in the composition, unless otherwise specified.

<Cellulose Particles>

Cellulose particles according to the present exemplary embodiment are solid (dense) cellulose particles containing cellulose as a main component and having a volume average particle diameter D of from 1 μm to 30 μm inclusive and a circularity of 0.86 or more, and a value A represented by formula (1) described later is less than 0.15.

The cellulose particles according to the present exemplary embodiment that have the structure described above have good spreadability, adsorption ability, and sustained component release performance. The reason for this may be as follows.

The cellulose particles are highly biodegradable and robust and are therefore expected to be used as a substitute for resin particles in various fields including cosmetic applications. Moreover, as the functionality of products in these applications increases, there is a need for the cellulose particles to have various functions.

The functions of the cellulose particles include spreadability and adsorption ability. When the cellulose particles have high spreadability and are applied to cosmetics, the cosmetics themselves spread well, and a smooth skin feel is obtained. Moreover, when the adsorption ability is high, the cosmetics obtained have high ability to adsorb components (such as sebum, sweat, and active ingredients of the cosmetics).

For example, porous spherical cellulose particles in Japanese Unexamined Patent Application Publication No. 2-222401 are known to have a good skin feel and good adsorption ability. These porous cellulose particles have high ability to adsorb components (such as sebum, sweat, and active ingredients of the cosmetics). However, since the components are incorporated into the particles, the sustained component release performance is low. Similarly, cellulose particles having a large number of voids have low sustained component release performance. When the sustained component release performance is low, the moist feel when the cellulose particles are used in cosmetic applications deteriorates.

However, the cellulose particles according to the present exemplary embodiment are solid (dense) and have a volume average particle diameter D of from 1 μm to 30 μm inclusive and a circularity of 0.86 or more, and the value A represented by formula (1) is less than 0.15. The cellulose particles having these properties have a solid structure, and components are less likely to be incorporated into these cellulose particles. Moreover, the value A represented by formula (1) is an indicator indicating the degree of irregularity of an irregular structure on the surface of the particles. The smaller the value A, the larger the degree of irregularity of the irregular structure on the surface of the particles. Therefore, by reducing the value A, the degree of irregularity of the irregular structure on the surface of the particles increases, and the components are more likely to be accumulated in concave portions. In this case, not only the adsorption ability but also the sustained release performance is improved.

When the particle surface has the irregular structure, the area of contact between the particles is small, and the particles are easily loosened, so that the spreadability is also improved.

When the volume average particle diameter is within the above range, the surface area of the particles is large. In this case, the adsorption ability and also the sustained release performance are further improved, and the cellulose particles can roll easily, so that the spreadability is further improved.

This may be the reason that the cellulose particles according to the present exemplary embodiment having the structure described above have good spreadability, adsorption ability, and sustained component release performance.

(Volume Average Particle Diameter)

The volume average particle diameter of the cellulose particles according to the present exemplary embodiment may be from 1 μm to 30 μm inclusive.

When the volume average particle diameter of the cellulose particles is 1 μm or more, the cellulose particles are unlikely to aggregate and can roll easily, and therefore the spreadability is improved. When the volume average particle diameter of the cellulose particles is 30 μm or less, the surface area of the particles is large, and the adsorption ability and also the sustained release performance are further improved. Therefore, the volume average particle diameter of the cellulose particles is set to be in the above range.

The volume average particle diameter of the cellulose particles is more preferably from 2 μm to 20 μm inclusive and still more preferably from 3 μm to 10 μm inclusive.

The volume average particle diameter of the cellulose particles is measured as follows.

An LS particle diameter distribution measurement apparatus "Beckman Coulter 1513 320 (manufactured by Beckman Coulter)" is used to measure the diameters of particles, and a cumulative particle diameter distribution is drawn from the small diameter side. A particle diameter at a cumulative frequency of 50% is determined as the volume average particle diameter.

(Value A Represented by Formula (1))

In the cellulose particles according to the present exemplary embodiment, the value A represented by formula (1) below is less than 0.15.

$$A = 1/(D \times S) \qquad \text{Formula (1)}$$

(in formula (1), D is the volume average particle diameter (μm) of the cellulose particles, and S is the BET specific surface area ($m^2/g$) of the cellulose particles).

When the value A represented by formula (1) is large, the surface of the cellulose particles is smooth, and the degree of irregularity of the irregular structure is small. In this case, the adsorption ability and the sustained component release performance deteriorate. Therefore, the value A represented by formula (1) is set to be in the above range.

The value A represented by formula (1) is preferably 0.13 or less and more preferably 0.1 or less. However, from the viewpoint of the sustained release performance, specifically, from the viewpoint that the sustained release performance deteriorates when the degree of irregularity of the surface of the particles is excessively large, the value A represented by formula (1) may be 0.05 or more.

(BET Specific Surface Area)

The BET specific surface area of the cellulose particles according to the present exemplary embodiment is preferably from 0.25 $m^2/g$ to 7 $m^2/g$ inclusive, more preferably from 0.5 $m^2/g$ to 5 $m^2/g$ inclusive, and still more preferably from 1 $m^2/g$ to 4 $m^2/g$ inclusive.

When the BET specific surface area of the cellulose particles is within the above range, the adsorption ability is improved while sufficient sustained component release performance is maintained.

The BET specific surface area of the cellulose particles is measured using a specific surface area measurement apparatus "Macsorb HM model-1201" manufactured by Mountech Co., Ltd.

Specifically, 50 mg of particles are subjected to pretreatment at 30° C. for 120 minutes, and then the BET specific surface area is determined by a BET multi-point method using nitrogen gas with a purity of 99.99% or higher.

(Circularity)

The circularity of the cellulose particles according to the present exemplary embodiment is 0.86 or more and is preferably 0.88 or more, more preferably 0.89 or more, and still more preferably 0.9 or more.

When the circularity of the cellulose particles is 0.86 or more (particularly 0.88 or more), the cellulose particles are close to spheres and can roll easily. Therefore, the spreadability is improved.

The circularity of the cellulose particles is ideally 1.

The circularity of a cellulose particle is determined as (the peripheral length of the equivalent circle of the cellulose particle)/(the peripheral length of the cellulose particle) [i.e., (the peripheral length of a circle having the same area as a projection image of the particle)/(the peripheral length of the projection image of the particle)]. Specifically, the average circularity is a value measured by the following method.

First, the cellulose particles used for the measurement are collected by suction, and a flattened flow of the particles is formed. Particle images are captured as still images using flashes of light, and the average circularity is determined by subjecting the particle images to image analysis using a flow-type particle image analyzer (FPIA-3000 manufactured by SYSMEX Corporation). The number of particles sampled for determination of the average circularity is 3500, and the arithmetic average is computed.

(Solidity)

The solidity of the cellulose particles according to the present exemplary embodiment is preferably 90% or more and more preferably 95% or more. The solidity of the cellulose particles is ideally 100%.

When the solidity of the cellulose particles is high, components are less likely to be incorporated into the particles, and therefore the sustained component release performance increases.

The solidity of the cellulose particles is measured as follows.

The cellulose particles are embedded in an epoxy resin and cut using, for example, a diamond knife to produce a specimen having an observation surface on which cross sections of the cellulose particles appear.

An SEM image of the cross section of a cellulose particle taken using a scanning electron microscope (SEM) is subjected to image analysis to compute the ratio of the area of the portion filled with the resin (i.e., cellulose) to the total area of the cross section of the cellulose particle.

Then the ratio of the area of the portion filled with the resin (i.e., cellulose) is measured in cross sections of ten or more randomly selected cellulose particles, and the average of the ratios is used as the solidity (area %).

(Cellulose)

The cellulose particles according to the present exemplary embodiment contain cellulose as a main component.

The phrase "contain cellulose as a main component" means that the content of cellulose with respect to the mass of the cellulose particles is 90% by mass or more.

When the cellulose particles each include a coating layer and an intermediate layer described later, the phrase "contain cellulose as a main component" means that the content of cellulose with respect to the mass of base particles is 90% by mass or more.

The number average molecular weight of the cellulose is preferably 37000 or more and more preferably 45000 or more.

No particular limitation is imposed on the upper limit of the number average molecular weight of the cellulose, and the upper limit may be 100000 or less.

When the number average molecular weight of the cellulose is 37000 or more, the cellulose particles obtained can more easily have good spreadability, adsorption ability, and sustained component release performance. Moreover, the biodegradability of the cellulose particles is improved. The reason for this may be as follows.

When the number average molecular weight of the cellulose is 37000 or more, the number of terminal hydroxy groups per unit volume of the particles decreases, and the number of intramolecular and extramolecular hydrogen bonds decreases. In this case, the cellulose particles are unlikely to aggregate. Therefore, the spreadability, the adsorption ability, and the sustained component release performance are improved.

Since the aggregation of the cellulose particles is suppressed, the specific surface area increases, and the biodegradability is also improved.

The number average molecular weight of the cellulose is measured by gel permeation chromatography (differential refractometer: Optilab T-rEX manufactured by Wyatt Technology, multi angle light scattering detector: DAWN HELEOS II manufactured by Wyatt Technology, columns: one TSKgel α-M and one TSKgel α-3000 manufactured by TOSOH Corporation) using dimethylacetamide (with 0.1M lithium chloride added thereto) as a solvent.

(Additional Components)

The cellulose particles according to the present exemplary embodiment may contain additional components. However, when the cellulose particles include a coating layer described later, the additional components are contained in base particles coated with the coating layer.

Examples of the additional components include a plasticizer, a flame retardant, a compatibilizer, a release agent, a light-resisting agent, a weather-resisting agent, a coloring agent, a pigment, a modifier, a dripping inhibitor, an antistatic agent, an anti-hydrolysis agent, a filler, reinforcing agents (such as glass fibers, carbon fibers, talc, clay, mica, glass flakes, milled glass, glass beads, crystalline silica, alumina, silicon nitride, aluminum nitride, and boron nitride), acid acceptors for preventing release of acetic acid (oxides such as magnesium oxide and aluminum oxide; metal hydroxides such as magnesium hydroxide, calcium hydroxide, aluminum hydroxide, and hydrotalcite; calcium carbonate; and talc), and reactive trapping agents (such as epoxy compounds, acid anhydride compounds, and carbodiimides).

The content of each additional component with respect to the total mass of the cellulose particles (or the base particles) may be from 0% by mass to 5% by mass inclusive. The term "0% by mass" means that the corresponding additional component is not contained.

(Particle Structure)

The cellulose particles according to the present exemplary embodiment may be cellulose particles including no coating layer. Specifically, the cellulose particles according to the present exemplary embodiment may be cellulose particles containing cellulose as a main component and having a single layer structure.

In the cellulose particles containing cellulose as a main component and having a single layer structure, the hydrophilic cellulose is exposed at the surface. Therefore, the ability to adsorb hydrophilic components (such as glycerin, hyaluronic acid, and amino acids) is enhanced, and sustained hydrophilic component release performance is improved.

—External Additive—

Inorganic particles may be externally added to the cellulose particles according to the present exemplary embodiment. When the inorganic particles are externally added, secondary aggregation of the particles is prevented, and therefore the particles can easily exert their intrinsic properties. Therefore, the spreadability, the adsorption ability, and the sustained component release performance can be easily improved. Moreover, a reduction in biodegradability may be prevented.

The external additive may be at least one selected from the group consisting of silicon-containing compound particles and metal oxide particles.

The silicon-containing compound particles are particles containing silicon.

The silicon-containing compound particles may be particles containing only silicon or may be particles containing silicon and other elements.

The silicon-containing compound particles may be silica particles. The silica particles may be particles containing silica, i.e., $SiO_2$, as a main component and may be crystalline or amorphous. The silica particles may be particles produced using a silicon compound such as water glass or alkoxysilane as a raw material or may be particles obtained by pulverizing quartz.

An oxide of a metal other than silicon can be used as the metal oxide.

Examples of the metal oxide include zinc oxide, magnesium oxide, iron oxide, and aluminum oxide.

From the viewpoint of a feel (specifically, a texture), the volume average particle diameter of the external additive is preferably from 1 nm to 100 nm inclusive and more preferably from 5 nm to 30 nm inclusive.

The volume average particle diameter of the external additive is measured using the same method as the method for measuring the volume average particle diameter of cellulose.

The amount of the external additive added externally may be from 0.1% by mass to 2% by mass inclusive with respect to the total mass of the cellulose particles (the cellulose particles with no external additive externally added thereto).

<Method for Producing Cellulose Particles>

A method for producing the cellulose particles according to the present exemplary embodiment is, for example, as follows.

—Process of Producing Cellulose Particles (Base Particles)—

(1) First, cellulose acylate is dissolved in a solvent mixture of a water-soluble organic solvent A and a water-soluble organic solvent B, and an organic solvent C is optionally added to prepare a cellulose acylate solution A. When the organic solvent C is added, pores are formed in the particles, and the solidity decreases.

(2) Next, the cellulose acylate solution A is added to a calcium carbonate dispersion obtained by dispersing calcium carbonate in water, and the mixture is stirred to prepare a cellulose acylate solution B.

(3) Next, the cellulose acylate solution B is added to a solution mixture of carboxymethyl cellulose and water to prepare a cellulose acylate solution C.

(4) Next, the cellulose acylate solution C is heated to remove the water-soluble organic solvents A and B. Then hydrochloric acid is added, and methanol is added to form cellulose acylate particles. Then the cellulose acylate particles are separated by filtration. The separated cellulose acylate particles are dispersed in water to prepare a cellulose acylate particle dispersion.

(5) Next, sodium hydroxide is added to the cellulose acylate particle dispersion. The resulting cellulose acylate particle dispersion is heated in a weak alkaline environment and stirred to saponify the cellulose acylate particles, and a cellulose particle suspension is thereby prepared.

(6) Next, hydrochloric acid is added to the cellulose particle suspension to adjust the pH of the suspension to near neutral (e.g., in the range of from 6.5 to 7 inclusive). Then the cellulose particles are repeatedly separated by filtration and washed with pure water. When the conductivity of the filtrate becomes 10 μs/cm or less, the cellulose particles separated by filtration are dried.

In the above production process, by adjusting the mass ratio of the water-soluble organic solvent A, the water-soluble organic solvent B, and the organic solvent C in the solvent mixture dissolving cellulose acylate, the value A represented by formula (1), BET specific surface area, solidity, etc. of the cellulose particles can be controlled.

By adjusting the amount of carboxymethyl cellulose, the volume average particle diameter of the cellulose particles can be controlled.

By adjusting the hydrophilicity and hydrophobicity of the cellulose acylate, the circularity of the cellulose particles can be controlled.

By controlling these properties, the cellulose particles according to the present exemplary embodiment are obtained.

The cellulose acylate is a cellulose derivative obtained by replacing at least one hydroxy group in cellulose with an aliphatic acyl group (acylating the cellulose). Specifically, the cellulose acylate is a cellulose derivative in which at least one hydroxy group in the cellulose is replaced with —CO—$R^{AC}$ ($R^{AC}$ represents an aliphatic hydrocarbon group).

The water-soluble organic solvent A is a solvent that allows 0.1% by mass to 10% by mass of water to dissolve therein at 25° C., and example thereof include ethyl acetate and butyl acetate.

The water-soluble organic solvent B is a solvent that allows 0.1% by mass to 30% by mass of water to dissolve therein at 25° C., and examples thereof include methyl ethyl ketone and methyl formate.

Examples of the organic solvent C include heptanol and octanol.

—Process of Forming Intermediate Layer and Coating Layer—

When the cellulose particles produced include the coating layer, the process of forming the coating layer (a coating layer forming process) may be performed after the cellulose particle (base particle) production process.

When the coating layer forming process is performed, the particles obtained through the cellulose particle (base particle) production process are used as base particles, and the coating layer is formed thereon.

First, a water dispersion containing the base particles dispersed therein is prepared. The base particles may be washed with an acid before the preparation of the water dispersion.

Next, the water dispersion containing the base particles dispersed therein is mixed with an aqueous solution containing a compound forming the intermediate layer. In this manner, for example, hydroxy groups of the resin contained in the base particles react with amine sites, carboxyl groups, amino groups, etc. of the compound forming the intermediate layer, or the hydroxy groups form hydrogen bonds, and the intermediate layer is thereby formed. The water dispersion in which the base particles having the intermediate layer formed thereon are dispersed is mixed with an emulsion containing a compound forming the coating layer. The coating layer is thereby formed.

When the intermediate layer is not formed, a water dispersion in which the base particles obtained through the cellulose particles (base particle) production process are dispersed is mixed with an emulsion containing the compound forming the coating layer to form the coating layer.

Then the cellulose particles having the coating layer are separated from the solution mixture. To separate the cellulose particles having the coating layer, the solution mixture is subjected to, for example, filtration. The separated cellulose particles having the coating layer may be washed with water. In this manner, an unreacted surface treating polymer can be removed. Then the cellulose particles having the coating layer are dried, and the cellulose particles according to the present exemplary embodiment are thereby obtained.

—External Addition Process—

An external additive may be added to the obtained cellulose particles.

The external addition process may be, for example, treatment in which the external additive is added to the cellulose particles using a mixing mill, a V blender, a Henschel mixer, a Loedige mixer, etc.

<Applications>

Examples of the application of the cellulose particles according to the present exemplary embodiment include granular materials such as cosmetics, rolling materials, abrasives, scrubbing agents, display spacers, materials for bead molding, light diffusing particles, resin strengthening agents, refractive index control agents, biodegradation accelerators, fertilizers, water-absorbent particles, toner particles, and anti-blocking particles.

The application of the cellulose particles according to the present exemplary embodiment may be cosmetics.

In particular, the application of the cellulose particles according to the present exemplary embodiment may be an additive for cosmetics.

The cellulose particles according to the present exemplary embodiment are applicable to, for example, additives for cosmetics such as base makeup cosmetics (such as makeup bases, concealers, foundations, and face powders), makeup cosmetics (such as lipsticks, glosses, lip liners, cheek cosmetics, eye shadows, eyeliners, mascaras, eyebrow cosmetics, nail polishes, and nail care cosmetics), and skin care cosmetics (such as facial cleansers, cleansing creams, lotions, emulsions, liquid foundations, face packs, face masks, and eye and mouth care cosmetics).

In particular, the cellulose particles according to the present exemplary embodiment may be used as cosmetic additives for makeup cosmetics because the cosmetic additives for makeup cosmetics are required to have flexibility and biodegradability.

EXAMPLES

Examples will next be described. However, the present disclosure is not limited to these Examples. In the following description, "parts" and "%" are based on mass, unless otherwise specified.

<Preparation of Materials>

The following materials are prepared.

(Cellulose Acylate)

CA-1: Diacetyl cellulose, "L50" manufactured by Daicel Corporation, number average molecular weight: 58000

CA-2: Cellulose acetate propionate, "CAP482-0.5" Eastman Chemical Company, number average molecular weight: 25000

Examples 1 to 9

—Formation of Base Particles—

A cellulose acylate of a type shown in Table 1 in an amount shown in Table 1 is dissolved in a solvent mixture of ethyl acetate and methyl ethyl ketone (MEK) mixed in amounts shown in Table 1 or a solvent mixture of ethyl acetate, methyl ethyl ketone (MEK), and heptanol mixed in amounts shown in Table 1. The resulting solution is added to a dispersion prepared by dispersing calcium carbonate in an amount shown in Table 1 in 500 parts of pure water, and the resulting mixture is stirred for 3 hours. The resulting mixture is added to a dispersion prepared by dispersing carboxymethyl cellulose (CMC) in an amount shown in Table 1 in 600 parts of pure water, and the mixture is stirred at 80° C. for 3 hours to remove ethyl acetate and methyl ethyl ketone. 10 Parts of dilute hydrochloric acid is added to the mixture to dissolve calcium carbonate. In this case, when heptanol is used, methanol in an amount of 10 times the amount of heptanol is added. The residue is filtrated and re-dispersed in 900 parts of pure water to obtain a base particle slurry.

—Saponification of Base Particles—

17.5 Parts of 20% NaOH is added to 500 parts of the base particle slurry (solid content: 10%), and the mixture is stirred in an environment of 30° C. for 6 hours. Hydrochloric acid is added to the saponified slurry to adjust the pH to 7. Then filtration and washing are repeated, and washing is performed until the conductivity of the filtrate becomes 10 s/cm or less to thereby obtain cellulose particles. The obtained base particles are dried at 80° C. for 3 hours to remove the solvent. A base particle cake is thereby obtained.

Comparative Examples 1 to 4

The following commercial cellulose particles are used as cellulose particles in Comparative Examples 1 to 4.

Comparative Example 1: "CELLUFLOW C-25" JNC Corporation

Comparative Example 2: "CELLULOBEADS D-30" DAITO KASEI KOGYO CO., LTD.

Comparative Example 3: "CELLULOBEADS D-10" DAITO KASEI KOGYO CO., LTD.

Comparative Example 4: "CELLULOBEADS USF-X" DAITO KASEI KOGYO CO., LTD.

<Evaluation of Physical Properties>

(Properties of Particles)

The following properties of the cellulose particles obtained in the Examples are measured using the methods described above.

Volume average particle diameter of cellulose particles (denoted by "Particle diameter" in Table 1)

Value A of cellulose particles that is represented by formula (1)

BET specific surface area of cellulose particles

Circularity of cellulose particles

Solidity of cellulose particles

<Evaluation>

The spreadability, adsorption ability, and sustained component release performance of the cellulose particles in the Examples are evaluated as follows.

—Spreadability—

Ten female testers are selected, and 0.5 g of a cellulose particle sample is placed on the back of their hand and spread over the skin to rate the cellulose particle sample. Specifically, 10 is the best, and 0 is the worst. The arithmetic average of the rating scores by the ten testers is determined for evaluation.

—Adsorption Ability—

The amount of linseed oil absorbed by cellulose particles is measured. Specifically, the following is performed.

10 g of linseed oil and 1 g of the cellulose particles are mixed and centrifuged under the conditions of a rotation speed of 10,000 rpm for 30 minutes. The supernatant linseed oil is removed, and then the weight of the particles is measured. The oil absorption rate is computed using the following formula.

Formula $$\text{Oil absorption rate} = (\text{Increase in weight after centrifugation}/\text{Weight of particles before centrifugation}) \times 100$$

The adsorption ability is evaluated according to the following criteria.

A: 120%<oil absorption rate

B: 100%≤oil absorption rate<120%

C: 80%≤oil absorption rate<100%

D: oil absorption rate<80%

—Sustained Component Release Performance (Moist Feel)—

75 Parts of talc, 10 parts of mica, 10 parts of cellulose particles, 3 parts of titanium dioxide, and 2 parts of sodium hyaluronate are mixed to prepare a face powder. Ten female testers are selected, and 0.5 g of the face powder sample is applied to the back of their hand. After a lapse of one hour, the testers are asked to rate the moist feel. Specifically, 10 is the best, and 0 is the worst. The arithmetic average of the rating scores by the ten testers is determined

| | | Cellulose particles | | | | | | | Properties of particles | |
|---|---|---|---|---|---|---|---|---|---|---|
| | | | | Solvent mixture for dissolving raw material cellulose acylate | | | | | | |
| | | Raw material cellulose acylate | | Amount A of ethyl acetate/ | Amount B of MEK/ | Amount C of heptanol/ | Calcium carbonate | CMC | Particle diameter D | Value A represented by formula |
| | | Type | Amount | parts | parts | parts | Parts | Parts | μm | (1) |
| Example 1 | CP1 | CA-1 | 130 | 435 | 435 | 0 | 100 | 4 | 5 | 0.09 |
| Example 2 | CP2 | CA-1 | 130 | 610 | 260 | 0 | 100 | 5 | 3.5 | 0.13 |
| Example 3 | CP3 | CA-1 | 130 | 260 | 610 | 0 | 100 | 2 | 15 | 0.07 |
| Example 4 | CP4 | CA-3 | 90 | 270 | 640 | 0 | 130 | 4 | 3.2 | 0.08 |
| Example 5 | CP5 | CA-1 | 130 | 435 | 435 | 0 | 90 | 0.6 | 25 | 0.09 |
| Example 6 | CP6 | CA-1 | 130 | 500 | 370 | 0 | 110 | 10 | 1.8 | 0.1 |
| Example 7 | CP7 | CA-1 | 130 | 395 | 395 | 80 | 100 | 3 | 9 | 0.09 |
| Example 8 | CP8 | CA-1 | 130 | 490 | 360 | 20 | 100 | 3.5 | 7 | 0.1 |
| Example 9 | CP9 | CA-2 | 110 | 510 | 380 | 0 | 100 | 4.5 | 4 | 0.1 |
| Comparative Example 1 | C-25 | "CELLUFLOW C-25" JNC Corporation | | | | | | | 9.7 | 0.07 |
| Comparative Example 2 | D-30 | "CELLULOBEADS D-30" DAITO KASEI KOGYO CO., LTD. | | | | | | | 32.3 | 0.13 |
| Comparative Example 3 | D-10 | "CELLULOBEADS D-10" DAITO KASEI KOGYO CO., LTD. | | | | | | | 14.2 | 0.18 |
| Comparative Example 4 | USF-X | "CELLULOBEADS USF-X" DAITO KASEI KOG YO CO., LTD. | | | | | | | 7.7 | 0.09 |

| | Properties of particles | | | Evaluation | | |
|---|---|---|---|---|---|---|
| | BET specific surface area $m^2/g$ | Circularity | Solidity % | Spreadability | Adsorption ability | Sustained release performance (moist feel) |
| Example 1 | 2.2 | 0.93 | 96 | 9 | A | 9 |
| Example 2 | 2.2 | 0.91 | 97 | 8 | A | 8 |
| Example 3 | 1.0 | 0.95 | 95 | 9 | A | 9 |
| Example 4 | 3.9 | 0.87 | 98 | 7 | A | 8 |
| Example 5 | 0.4 | 0.97 | 95 | 9 | B | 7 |
| Example 6 | 5.6 | 0.9 | 98 | 7 | A | 9 |
| Example 7 | 1.2 | 0.93 | 80 | 9 | A | 7 |
| Example 8 | 1.4 | 0.92 | 92 | 9 | A | 8 |
| Example 9 | 2.5 | 0.89 | 95 | 8 | A | 9 |
| Comparative Example 1 | 1.5 | 0.91 | 60 | 6 | A | 2 |
| Comparative Example 2 | 0.2 | 0.93 | 95 | 7 | D | 3 |
| Comparative Example 3 | 0.4 | 0.95 | 94 | 7 | D | 3 |
| Comparative Example 4 | 1.4 | 0.85 | 96 | 3 | C | 4 |

As can be seen from the above results, the cellulose particles in the Examples have better spreadability, adsorption ability, and sustained component release performance than the cellulose particles in the Comparative Examples.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

APPENDIX (((1)))

Solid cellulose particles containing cellulose as a main component, wherein the cellulose particles have a volume average particle diameter D of from 1 μm to 30 μm inclusive and a circularity of 0.86 or more, and wherein a value A represented by the following formula (1) is less than 0.15:

$$A = 1/(D \times S) \quad \text{formula (1)}$$

(wherein, in formula (1), D is the volume average particle diameter (μm) of the cellulose particles, and S is a BET specific surface area ($m^2/g$) of the cellulose particles).

(((2)))

The cellulose particles according to (((1))), wherein the volume average particle diameter is from 2 μm to 20 μm inclusive.

(((3)))

The cellulose particles according to (((1))) or (((2))), wherein the value A represented by formula (1) is 0.1 or less.

(((4)))

The cellulose particles according to any one of (((1))) to (((3))), wherein the BET specific surface area is from 0.25 $m^2/g$ to 7 $m^2/g$ inclusive.

(((5)))

The cellulose particles according to (((4))), wherein the BET specific surface area is from 0.5 $m^2/g$ to 5 $m^2/g$ inclusive.

(((6)))

The cellulose particles according to any one of (((1))) to (((5))), wherein the circularity is 0.88 or more.

(((7)))

The cellulose particles according to (((6))), wherein the circularity is 0.9 or more.

(((8)))

The cellulose particles according to any one of (((1))) to (((7))), wherein the cellulose particles have a solidity of 90% or more.

(((9)))

The cellulose particles according to (((8))), wherein the solidity is 95% or more.

(((10)))

The cellulose particles according to any one of (((1))) to (((8))), wherein the BET specific surface area is from 0.25 $m^2/g$ to 7 $m^2/g$ inclusive, wherein the circularity is 0.88 or more, and wherein the cellulose particles have a solidity of 90% or more.

(((11)))

The cellulose particles according to any one of (((1))) to (((8))), wherein the volume average particle diameter is from 2 μm to 20 μm inclusive, wherein the value A represented by formula (1) is less than 0.1, wherein the BET specific surface area is from 0.5 $m^2/g$ to 5 $m^2/g$ inclusive, wherein the circularity is 0.9 or more, and wherein the cellulose particles have a solidity of 95% or more.

What is claimed is:

1. Solid cellulose particles containing cellulose as a main component, wherein a content of the cellulose with respect to a mass of the cellulose particles is 90% by mass or more, wherein the cellulose particles have a volume average particle diameter D of from 1 μm to 30 μm inclusive and a circularity of 0.86 or more, wherein a value A represented by the following formula (1) is 0.05 or more and less than 0.15:

$$A = 1/(D \times S) \qquad \text{formula (1)}$$

wherein, in formula (1), D is the volume average particle diameter of the cellulose particles in μm, and S is a BET specific surface area of the cellulose particles in $m^2/g$, and wherein the cellulose particles have a solidity of 90% or more.

2. The cellulose particles according to claim 1, wherein the volume average particle diameter is from 2 μm to 20 μm inclusive.

3. The cellulose particles according to claim 1, wherein the value A represented by formula (1) is 0.05 or more and 0.1 or less.

4. The cellulose particles according to claim 1, wherein the BET specific surface area is from 0.25 $m^2/g$ to 7 $m^2/g$ inclusive.

5. The cellulose particles according to claim 4, wherein the BET specific surface area is from 0.5 $m^2/g$ to 5 $m^2/g$ inclusive.

6. The cellulose particles according to claim 1, wherein the circularity is 0.88 or more.

7. The cellulose particles according to claim 6, wherein the circularity is 0.9 or more.

8. The cellulose particles according to claim 1, wherein the solidity is 95% or more.

9. The cellulose particles according to claim 1, wherein the BET specific surface area is from 0.25 $m^2/g$ to 7 $m^2/g$ inclusive, and wherein the circularity is 0.88 or more.

10. The cellulose particles according to claim 1, wherein the volume average particle diameter is from 2 μm to 20 μm inclusive, wherein the value A represented by formula (1) is 0.05 or more and less than 0.1, wherein the BET specific surface area is from 0.5 $m^2/g$ to 5 $m^2/g$ inclusive, wherein the circularity is 0.9 or more, and wherein the solidity is 95% or more.

* * * * *